United States Patent [19]
Hayes

[11] Patent Number: 5,387,241
[45] Date of Patent: Feb. 7, 1995

[54] RIBBED AUGMENT FOR A PROSTHETIC IMPLANT

[75] Inventor: Kevin B. Hayes, Milford, Ind.

[73] Assignee: Zimmer, Inc., Warsaw, Ind.

[21] Appl. No.: 190,744

[22] Filed: Jan. 28, 1994

[51] Int. Cl.6 .............................................. A61F 2/38
[52] U.S. Cl. .................................. 623/20; 623/18
[58] Field of Search ........................... 623/16, 18, 20

[56] References Cited

U.S. PATENT DOCUMENTS

| | | | |
|---|---|---|---|
| 4,281,420 | 8/1981 | Raab | 3/1.912 |
| 4,336,618 | 6/1982 | Raab | 3/1.913 |
| 4,491,987 | 1/1985 | Park | 3/1.91 |
| 4,731,086 | 3/1988 | Whiteside et al. | 623/20 |
| 4,769,039 | 9/1988 | Horber | 623/20 |
| 4,842,606 | 6/1989 | Kranz et al. | 623/23 |
| 4,911,721 | 3/1990 | Branemark et al. | 623/20 |
| 4,936,847 | 6/1990 | Manginelli | 623/23 |
| 4,944,757 | 7/1990 | Martinez et al. | 623/20 |
| 4,950,298 | 8/1990 | Gustilo et al. | 623/20 |
| 4,995,883 | 2/1991 | Demane et al. | 623/23 |
| 5,019,103 | 5/1991 | Van Zile et al. | 623/20 |
| 5,047,058 | 9/1991 | Roberts et al. | 623/20 |
| 5,152,797 | 10/1992 | Luckman et al. | 623/20 |

FOREIGN PATENT DOCUMENTS 2259253A 3/1993 United Kingdom ........... A61F 2/02

OTHER PUBLICATIONS

Zimmer, Inc.—Insall/Burnstein II Modular Knee System—Catalog pp. 175–176, 1991.
Allo Pro Corporation—A GSB "taylor-made" Prosthesis—JBJS—Mar. 1986.
Johnson & Johnson Orthopaedics—P.F.C. Modular Total Knee System—No date avail.
Osteonics—Osteonics Series 7000 Total Knee System—JBJS Dec. 1993.
Zimmer, Inc. Brochure—Insall/Burnstein II Modular Knee System—1993.

Primary Examiner—David Isabella
Assistant Examiner—Debra S. Brittingham
Attorney, Agent, or Firm—Margaret L. Geringer

[57] ABSTRACT

A prosthetic joint implant for replacing a portion of a bone having a base member 10 with a first surface 11 for positioning toward a surface of the bone. The first surface 11 includes a shallow recessed portion 13 and a raised peripheral rim 14 at an outer edge 15 of the recessed portion. The joint implant 1 further includes a separate augment member 40 having a first face 41 adapted to be selectively positioned against the first surface 11 of base member 10. The first face 41 includes a peripheral outer edge 43 thereabout and an elongated raised rib 44 having an outer shoulder 45 which abuts an inner shoulder 16 of raised rim 14 of base member 10. The raised rib 44 of augment member 40 extends only about halfway or less around the peripheral outer edge 43 of augment member 40. The raised rib 44 provides resistance to shear forces that act toward the direction of the rib 44 positioned along an outer side of the base member 10 when the augment member is connected thereto.

6 Claims, 2 Drawing Sheets

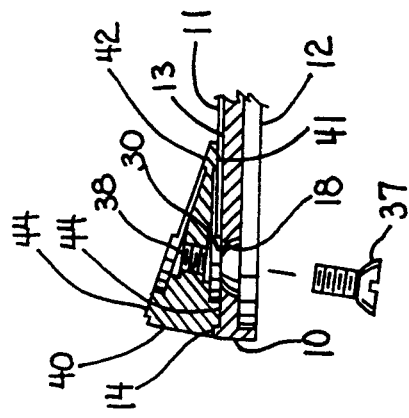
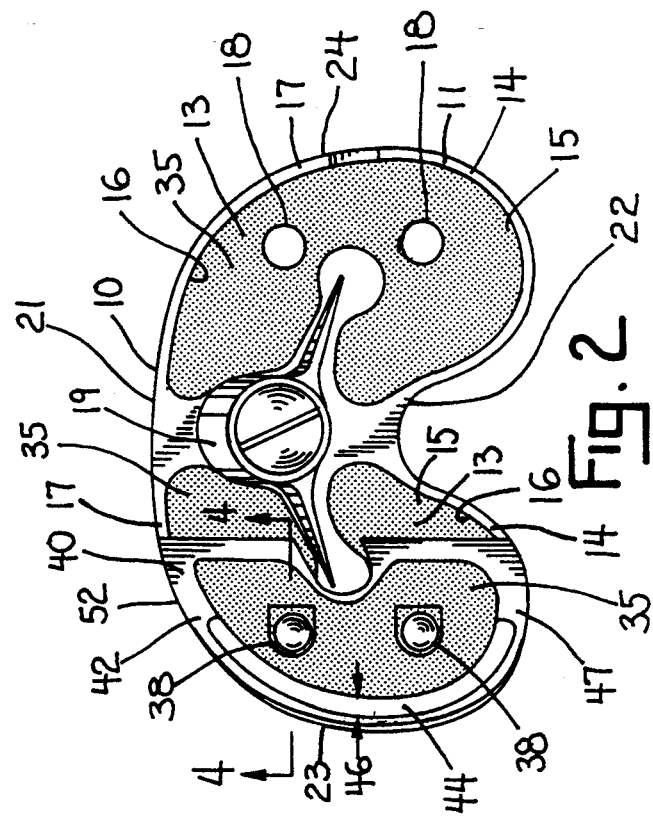
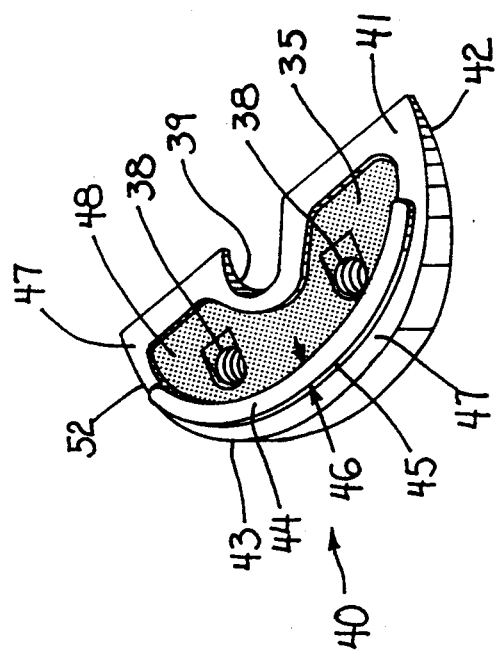
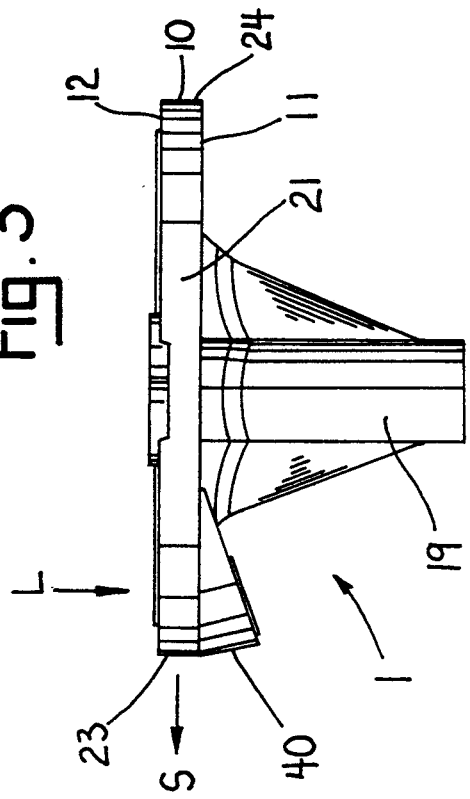

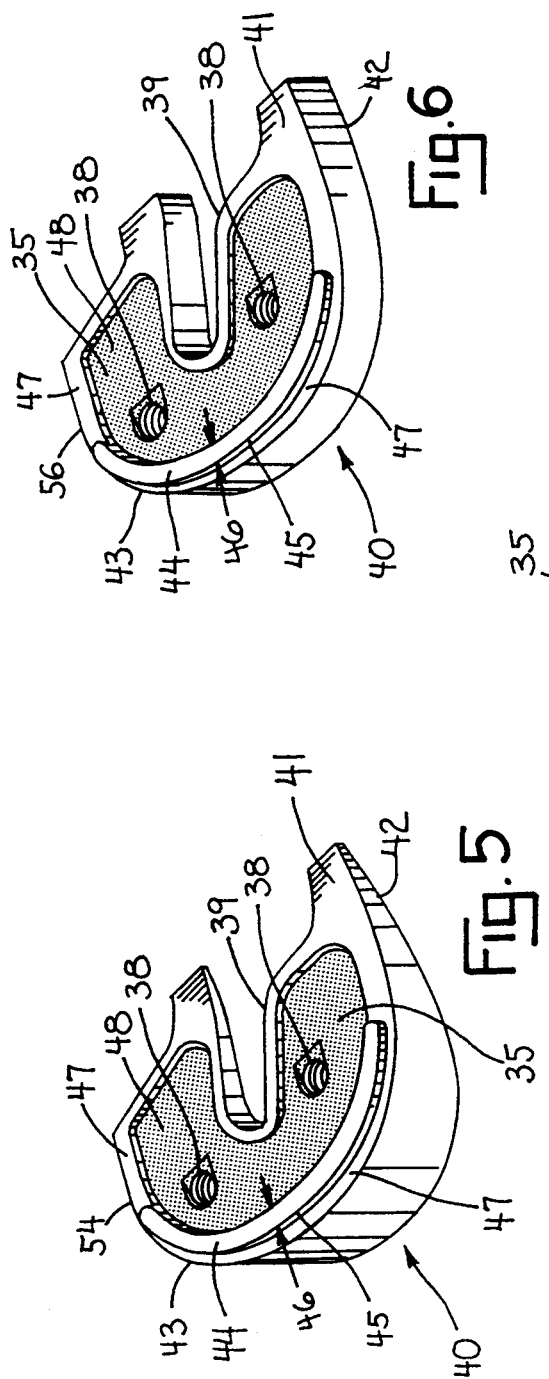
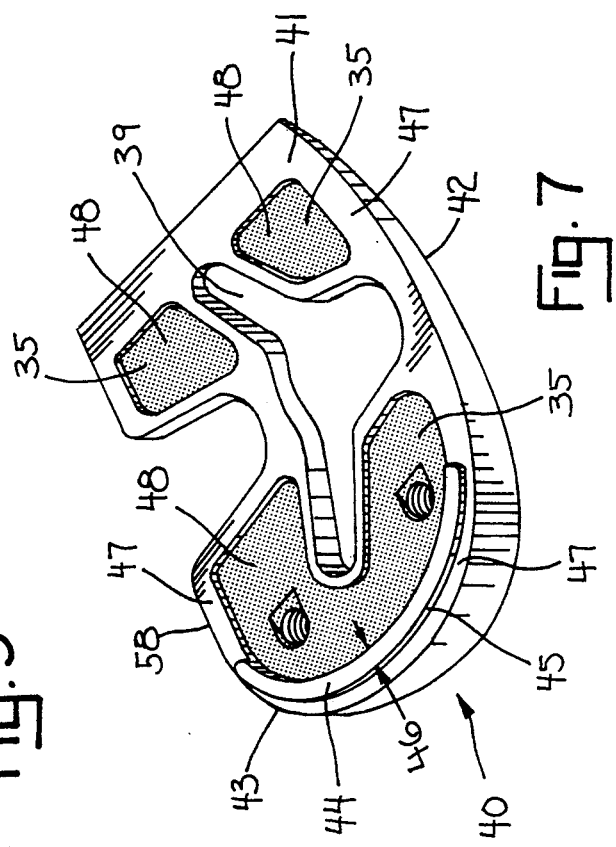

RIBBED AUGMENT FOR A PROSTHETIC IMPLANT

FIELD OF THE INVENTION

This invention relates to a modular prosthetic implant system. In particular, this invention relates to such a system which includes modular augment components.

BACKGROUND OF THE INVENTION

While this invention is particularly suitable for modular tibial prosthesis components having modular augment members, the features of this invention could be adapted, as appropriate, to other prosthetic components which utilize modular augment members.

It is well known in the art to utilize modular augment members to provide an additional thickness of material onto the base implant. The following patents disclose the use of various modular augment type members which are attached in various ways to a base implant component: U.S. Pat. Nos. 5,152,797; 5,047,058; 5,019,103; 4,995,883; 4,950,298; 4,944,757; 4,936,847; 4,911,721; 4,842,606; 4,769,039; 4,731,086; and U.K. Patent Application GB 2 259 253A.

Numerous prosthetic implant systems are available commercially which include augment members including the following: The GSB Knee System sold by Allo Pro Corporation; The PFC Modular Total Knee System sold by Johnson & Johnson Orthopaedics; The Series 7000 Total Knee System sold by Osteonics; and the Insall/Burstein II Modular Knee System sold by Zimmer.

For those systems in which the base member includes a raised peripheral edge to engage a corresponding augment, the augment typically has a raised peripheral edge or raised platform which fully or substantially fully extends about the periphery of the augment.

In addition, the following three patents disclose representative examples of acrylic precoating of prosthetic implants which will be referred to later in the specification: U.S. Pat. Nos. 4,491,987; 4,336,618, and 4,281,420.

SUMMARY OF THE INVENTION

The present invention provides a prosthetic joint implant for replacing a portion of a bone having a base member with a first surface for positioning toward a surface of the bone. The first surface includes a shallow recessed portion and a raised peripheral rim at an outer edge of the recessed portion. The joint implant further includes a separate augment member having a first face adapted to be selectively positioned against the first surface of base member. The first face includes a peripheral outer edge thereabout and an elongated raised rib having an outer shoulder which abuts an inner shoulder of raised rim of base member. The raised rib of augment member extends only about halfway or less around the peripheral outer edge of the augment member.

Accordingly, it is an advantage of the present invention to provide a raised rib on an augment member which provides resistance to shear forces that act toward the direction of the rib positioned along an outer side of the base member when the augment member is connected thereto.

Another advantage of the invention is to provide a novel ribbed augment member in which the raised rib of the augment member extends only about halfway or less around the peripheral outer edge of the augment member.

A further advantage of the invention is to provide a preapplied coating of an acrylic material on both the undersurface of the base member as well as on an aligned surface of the augment member to enhance attachment to a selectively applied bonding material therebetween.

Still other advantages of the invention will become apparent upon reference to the accompanying drawings.

BRIEF DESCRIPTION OF THE DRAWINGS

FIG. 1 is a front elevational view of a tibial base member shown with a partial angled augment attached thereto in accordance with the present invention.

FIG. 2 is a bottom plan view of the tibial base member and the partial angled augment of FIG. 1.

FIG. 3 is a perspective view of the partial angled augment of FIG. 1.

FIG. 4 is a partial cross-sectional view taken along lines 4—4 of FIG. 2.

FIG. 5 is a perspective view of a half angled augment in accordance with the present invention.

FIG. 6 is a perspective view of a half flat augment in accordance with the present invention.

FIG. 7 is a perspective view of a full angled augment in accordance with the present invention.

DESCRIPTION OF THE PREFERRED EMBODIMENT

FIGS. 1–7 illustrate a particularly advantageous embodiment of the ribbed augment of the present invention. The invention will be described with reference to a modular prosthetic tibial component; however, it is understood that it is not limited thereto.

The modular prosthetic joint tibial implant component 1 has a base member 10 with a first surface 11 for positioning toward a surface of the bone. The base member 10 also includes a second surface 12, which for tibial component 1, typically is adapted to engage a mating tibial articular surface (not shown), as is well known in the art and which can be secured to second surface 12 in any suitable manner. The first surface 11 includes a shallow recessed portion 13 and a raised peripheral rim 14 at an outer edge 15 of the recessed portion. The joint implant 1 further includes a separate augment member 40 having a first face 41 adapted to be selectively positioned against the first surface 11 of base member 10. The first face 41 includes a peripheral outer edge 43 thereabout and an elongated raised rib 44 having an outer shoulder 45 which abuts an inner shoulder 16 of raised rim 14 of base member 10. The raised rib 44 of augment member 40 extends only about halfway or less around the peripheral outer edge 43 of augment member 40. The raised rib 44 provides resistance to shear forces "S" that act toward the direction of the rib 44 positioned along an outer side of the base member 10 when the augment member is connected thereto and under a load "L".

The first surface 11 of base member 10 includes an anterior side 21, and an oppositely located posterior side 22 and first and second connecting outer sides 23 and 24. The rib 44 of augment 40 extends only around one of the first and second connecting sides 23 and 24 of base member 10 when selectively positioned thereagainst. The rib 44 of augment 40 extends substantially the full length of said one of the first and second connecting sides 23 and 24, extending from the anterior side 21 to the posterior side 22, when selectively positioned against base member 10.

The elongated rib 44 is spaced inwardly from the peripheral outer edge 43 of first face 41 to form a lower border portion 47 between the peripheral outer edge 43 of first face 41 and the outer shoulder 45 of rib 44. The lower border portion 47 continues and extends substantially all around the peripheral outer edge 43 of augment 40. The first face 41 of augment 40 further includes a recessed inner portion 48 which is recessed relative to both the raised rib 44 and the lower border portion 47. The lower border portion 47 of augment 40 aligns with and abuts a bottom surface 17 of the raised peripheral rim 14 of base member 10 when augment 40 is selectively positioned against base member 10. The recessed portion 13 of the base member 10 and the recessed inner portion of augment 40 are aligned to form a chamber 30 for selectively receiving a bonding material (not shown) therebetween to secure the augment 40 to base member 10. The interengagement of the rim 14 and the rib 44 also helps to act as a cement dam when such cement is used between the augment 40 and the base 10.

The recessed inner portion 48 of first face 41 of augment 40 and the recessed portion 13 of the first surface 11 of base 10 may include a preapplied thin coating 35 of an acrylic material, such as that described in U.S. Pat. Nos. 4,491,987 or 4,336,618 or 4,281,430. This coating 35 will enhance attachment of the augment 40 and base 10 when a bonding material, such as any suitable bone cement or the like is selectively applied therebetween. The thin coating 35 is shown in FIGS. 2, 3, and 5-7 and is represented by the dot pattern. Coating 35 is not shown in the cross-section of FIG. 4 for clarity of the detail of FIG. 4.

The elongated raised rib 44 of augment 40 has a substantially uniform width 46 along its length, as well as a uniform thickness.

The base 10 may include an elongated stem portion 19 extending from first surface 11 of base 10. The augment 40 may include a corresponding cutout portion 39 for fitting about the stem portion 19, as is known in the art of modular augments.

It is noted that augment 40 includes a second face 42 oppositely located from first face 41 in which the second face 42 may be a mirror image of the first face 41, which is also known in the art of modular augments. This enables either one of the first or second faces 41 or 42 to be selectively positioned against the undersurface of the base 10. For example, with the partial angled augment 52 of FIGS. 1-4, FIGS. 1 and 2 show first face 41 against the first surface 11 of base 10. If the augment 10 were flipped over, it could be positioned on the opposite side of stem portion 19, but with second face 42 against the first surface 11 of base 10.

FIGS. 1-4 show a partial angled augment 52, while FIG. 5 shows a half angled augment 54 which extends about halfway across the first surface 11 of base 10. FIG. 6 shows a half flat augment, while FIG. 7 shows a full angled augment which extends substantially or almost all the way across the first surface 11 of base 10. It is also known in the art of modular augments to provide partial, half, or full augments, as well as, varied angles of augments and varied thicknesses of flat or angled augments. However, these variations are shown herein in order to illustrate the features of the present invention on the various styles of augments.

The base member 10 also may include holes 18 and the augment 40 may include corresponding threaded holes 38 which align with holes 18 in base 10 for selectively accepting a connecting screw 37 to further secure the augment 40 to base 10. It is known in the art of augments to utilize such connecting screws 37. It is also known to selectively apply a bonding material, such as a bone cement, between the augment 40 and base 10, if desired, to provide a securing of the augment to the base. Either the mechanical method, such as with screws 37, may be used or the bonding method, such as with bone cement, may be utilized to secure augment 40 to base 10. Both methods may be utilized in conjunction with each other, if desired.

The augment 40 and base member 10 may be made out of metal, such as a cobalt-chromium alloy or any suitable surgical grade material. Any suitable manufacturing methods may be utilized.

While this invention has been described in terms of a particularly advantageous embodiment, those skilled in the art can appreciate that modifications can be made without departing from the spirit and scope of this invention.

I claim:

1. A prosthetic joint implant for replacing a portion of a bone having a base member with a first surface for positioning toward a surface of the bone, said first surface comprising a shallow recessed portion and a raised peripheral rim at an outer edge of the recessed portion, said rim having an inner shoulder, and having a separate augment member having a first face adapted to be selectively positioned against the first surface of the base member and wherein the first face includes a peripheral outer edge thereabout and an elongated raised rib having an outer shoulder, which abuts the inner shoulder of the raised rim of the base member, and wherein the elongated raised rib is spaced inwardly from the peripheral outer edge to form a lower border portion between the peripheral outer edge of the first face and the outer shoulder of the rib, and wherein the raised rib extends only about halfway or less around the peripheral outer edge of the augment member, wherein the first surface of the base member includes an anterior side and an oppositely located posterior side and first and second connecting sides,and wherein the rib of the augment extends around only one of the first and second connecting sides of the first surface of the base member when selectively positioned thereagainst.

2. The implant of claim 1 wherein the rib of the augment extends along substantially the full length of said one of the first and second connecting sides, extending from the anterior side to the posterior side, when selectively positioned against the base member.

3. A prosthetic joint implant for replacing a portion of a bone having a base member with a first surface for positioning toward a surface of the bone, said first surface comprising a shallow recessed portion and a raised peripheral rim at an outer edge of the recessed portion, said rim having an inner shoulder, and having a separate augment member having a first face adapted to be selectively positioned against the first surface of the base member and wherein the first face includes a peripheral outer edge thereabout and an elongated raised rib having an outer shoulder, which abuts the inner shoulder of the raised rim of the base member, and wherein the elongated raised rib is spaced inwardly from the peripheral outer edge to form a lower border portion between the peripheral outer edge of the first face and the outer shoulder of the rib, and wherein the raised rib extends only about halfway or less around the peripheral outer edge of the augment member, wherein the elongated raised rib of the augment member has a substantially uniform width along its length.

4. A prosthetic joint implant for replacing a portion of a base having a base member with a first surface for positioning toward a surface of the bone, said first surface comprising a shallow recessed portion and a raised peripheral rim at an outer edge of the recessed portion, said rim having an inner shoulder, and having a separate augment member having a first face adapted to be selectively positioned against the first surface of the base member and wherein the first face includes a peripheral outer edge thereabout and an elongated raised rib having an outer shoulder, which abuts the inner shoulder of the raised rim of the base member, and wherein the raised rib extends only about halfway or less around the peripheral outer edge of the augment member, wherein the elongated raised rib is spaced inwardly from the peripheral outer edge to form a lower border portion between the peripheral outer edge of the first face and the outer shoulder of the rib and wherein the lower border portion continues and extends substantially all around the peripheral outer edge of the augment member, and wherein the first face of the augment member further includes a recessed inner portion which is recessed relative to both the raised rib and the lower border portion, and wherein the lower border portion of the augment member aligns with and abuts a bottom surface of the raised peripheral rim of the base member, when selectively positioned against the base member, and wherein the recessed portion of the base member and the recessed inner portion of the augment member are aligned to form a chamber for selectively receiving a bonding material therebetween to secure the augment member to the base member.

5. A prosthetic joint implant for replacing a portion of a bone having a base member with a first surface for positioning toward a surface of the bone, said first surface comprising a shallow recessed portion and a raised peripheral rim at an outer edge of the recessed portion, said rim having an inner shoulder, and having a separate augment member having a first face adapted to be selectively positioned against the first surface of the base member and wherein the first face includes a peripheral outer edge thereabout and an elongated raised rib having an outer shoulder, which abuts the inner shoulder of the raised rim of the base member, and wherein the raised rib extends only about halfway or less around the peripheral outer edge of the augment member, wherein at least a portion of the first face of the augment member and at least a portion of the recessed portion of the first surface of the base member includes a preapplied coating of an acrylic material to enhance attachment to a selectively applied bonding material therebetween.

6. A prosthetic joint implant for replacing a portion of a bone having a base member with a first surface for positioning toward a surface of the bone, said first surface comprising a shallow recessed portion and a raised peripheral rim at an outer edge of the recessed portion, said rim having an inner shoulder, and having a separate augment member having a first face adapted to be selectively positioned against the first surface of the base member and wherein the first face includes a peripheral outer edge thereabout and an elongated raised rib having an outer shoulder, which abuts the inner shoulder of the raised rim of the base member, and wherein at least a portion of the first face of the augment member and at least a portion of the recessed portion of the first surface of one base member includes a preapplied coating of an acrylic material to enhance attachment to a selectively applied bonding material therebetween.

* * * * *